(12) United States Patent
Hotta et al.

(10) Patent No.: US 10,772,340 B2
(45) Date of Patent: Sep. 15, 2020

(54) REFINED CHLOROGENIC ACID-CONTAINING COMPOSITION

(71) Applicant: KAO CORPORATION, Tokyo (JP)

(72) Inventors: Yusuke Hotta, Kashima (JP); Yukiteru Sugiyama, Narita (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/345,118

(22) PCT Filed: Sep. 28, 2017

(86) PCT No.: PCT/JP2017/035268
§ 371 (c)(1),
(2) Date: Apr. 25, 2019

(87) PCT Pub. No.: WO2018/079179
PCT Pub. Date: May 3, 2018

(65) Prior Publication Data
US 2019/0281855 A1 Sep. 19, 2019

(30) Foreign Application Priority Data
Oct. 26, 2016 (JP) ................... 2016-209199

(51) Int. Cl.
*A23F 5/26* (2006.01)
*C07C 67/56* (2006.01)
*A23L 33/105* (2016.01)
*C07C 69/618* (2006.01)
*A61P 17/18* (2006.01)
*A61P 43/00* (2006.01)
*A61P 9/12* (2006.01)
*C07C 69/732* (2006.01)
*A61K 31/216* (2006.01)
*A61P 1/16* (2006.01)
*A61K 36/74* (2006.01)

(52) U.S. Cl.
CPC ............. *A23F 5/26* (2013.01); *A23L 33/105* (2016.08); *A23V 2002/00* (2013.01); *A23V 2200/326* (2013.01); *A23V 2250/2132* (2013.01); *A61K 31/216* (2013.01); *A61K 36/74* (2013.01); *A61P 1/16* (2018.01); *A61P 9/12* (2018.01); *A61P 17/18* (2018.01); *A61P 43/00* (2018.01); *C07C 67/56* (2013.01); *C07C 69/618* (2013.01); *C07C 69/732* (2013.01)

(58) Field of Classification Search
None
See application file for complete search history.

(56) References Cited

U.S. PATENT DOCUMENTS

| | | |
|---|---|---|
| 4,048,345 A | 9/1977 | Katz |
| 5,702,747 A | 12/1997 | Sipos et al. |
| 9,029,588 B2 * | 5/2015 | Yamawaki ............... A23F 5/223 560/18 |
| 9,034,410 B2 | 5/2015 | Vella et al. |
| 2006/0210689 A1 * | 9/2006 | Velissariou ............ A23F 5/163 426/594 |
| 2008/0044539 A1 | 2/2008 | Perlman et al. |
| 2009/0092736 A1 | 4/2009 | Koyama et al. |
| 2012/0251678 A1 | 10/2012 | Leloup et al. |
| 2013/0131165 A1 * | 5/2013 | Sugiyama .................. A61P 9/12 514/533 |
| 2013/0230608 A1 | 9/2013 | Silber et al. |
| 2014/0271988 A1 * | 9/2014 | Robinson .................. A23F 5/18 426/45 |
| 2017/0013857 A1 | 1/2017 | Ozato |
| 2018/0160696 A1 | 6/2018 | Ozato et al. |

FOREIGN PATENT DOCUMENTS

| | | |
|---|---|---|
| EP | 0916267 A2 | 5/1999 |
| EP | 2592064 A1 | 5/2013 |
| EP | 2644036 A1 | 10/2013 |
| GB | 1488340 A | 10/1977 |
| JP | 2006-104070 A | 4/2006 |
| JP | 2006-174746 A | 7/2006 |
| JP | 2008-31150 A | 2/2008 |
| JP | 2008-266144 A | 11/2008 |
| JP | 2010-178664 A | 8/2010 |
| JP | 2011-182749 A | 9/2011 |
| JP | 2012-31165 A | 2/2012 |
| JP | 2013-138631 A | 7/2013 |
| JP | 2015-142565 A | 8/2015 |
| JP | 2016-106627 A | 6/2016 |
| JP | 6389940 B2 | 9/2018 |
| JP | 2019-000099 A | 1/2019 |
| WO | WO 2007/122796 A1 | 11/2007 |
| WO | WO 2012/005293 A1 | 1/2012 |

(Continued)

OTHER PUBLICATIONS

U.S. Office Action for U.S. Appl. No. 16/345,188, dated Aug. 22, 2019.
International Search Report (PCT/ISA/210) issued in PCT/JP2017/035268, dated Jan. 9, 2018.
U.S. Appl. No. 16/345,188, filed Apr. 25, 2019.
U.S. Appl. No. 16/345,194, filed Apr. 25, 2019.
International Search Report, dated Jan. 9, 2018, for International Application No. PCT/JP2017/035266, with an English translation.
International Search Report, dated Jan. 9, 2018, for International Application No. PCT/JP2017/035267, with an English translation.
Japanese Office Action, dated Apr. 6, 2018, for Japanese Application No. 2017-188160 with an English machine translation.
SUGI Blog, Sep. 6, 2014, retrived on Dec. 20, 2017, (https://ameblo.jp/sugichan0826/entry-11920899630.html) non-official translation (An Look at the ATAGO BRIX/TDS Scale), total of 7 pages.

(Continued)

*Primary Examiner* — Clinton A Brooks
*Assistant Examiner* — Kofi Adzamli
(74) *Attorney, Agent, or Firm* — Birch, Stewart, Kolasch & Birch, LLP

(57) ABSTRACT

Provided is a purified chlorogenic acid-containing composition, having: a content of a chlorogenic acid in solids of from 10 mass % to 70 mass %; a "glucose/chlorogenic acid" mass ratio of from 0.1 to 0.9; a "caffeine/chlorogenic acid" mass ratio of 0.05 or less; and a pH of from 1 to 5.

20 Claims, No Drawings

(56) References Cited

FOREIGN PATENT DOCUMENTS

| WO | WO 2014/155746 A1 | 10/2014 |
| WO | WO 2015/093522 A1 | 6/2015 |
| WO | WO 2016/031625 A1 | 3/2016 |

OTHER PUBLICATIONS

Author Unknown, "Carbohydrates in Coffee", URL: https:www.coffeechemistry.com/chemistry/carbohydrates/carbohydrates-in-coffee, XP055676898, Apr. 23, 2015, 5 pages.
Extended European Search Report, dated Mar. 23, 2020, for European Application No. 17863734.4.
Extended European Search Report, dated Mar. 25, 2020, for European Application No. 17865450.5.
U.S. Office Action, dated Jan. 17, 2020, for U.S. Appl. No. 16/345,168.
U.S. Office Action for U.S. Appl. No. 16/345,168, dated Jan. 17, 2020.
Extended European Search Report dated Jun. 9, 2020, for European Application No. 17864962.0.

* cited by examiner

REFINED CHLOROGENIC ACID-CONTAINING COMPOSITION

FIELD OF THE INVENTION

The present invention relates to a purified chlorogenic acid-containing composition.

BACKGROUND OF THE INVENTION

As materials having bioactive functions, there have been proposed a variety of materials. For example, there are given polyphenols as those having bioactive functions, such as an antioxidative effect, an antihypertensive effect, and a hepatic function-improving effect. A chlorogenic acid, which is one of the polyphenols, has been reported to have a high antihypertensive effect, and is expected to find applications in supplements and food and drink.

As a material containing a large amount of the chlorogenic acid, there are given coffee beans. A chlorogenic acid-containing composition obtained by extraction from the coffee beans has been conventionally investigated with regard to, for example, an increase in recovery rate of the chlorogenic acid, a reduction in impurities, such as caffeine, an improvement in taste and flavor, and an improvement in color. For example, as a method of producing a purified chlorogenic acid that is so stable as not to form precipitates immediately after production, and that does not form secondary precipitates even when an extract is subjected to heat sterilization, and further to long-term storage, there has been proposed a method involving concentrating a coffee extract to a refractive sugar content (20° C.) of Bx8° or more as solids concentration, and then bringing the concentrated extract into contact with acid clay and/or activated clay. It has been reported that the resulting purified chlorogenic acid has reductions in caffeine and solids through treatment, but does not change in composition of organic acids, such as malic acid and acetic acid, and has a refreshing taste and flavor without coarseness (Patent Document 1).

(Patent Document 1) JP-A-2008-266144

SUMMARY OF THE INVENTION

The present invention provides a purified chlorogenic acid-containing composition, having: a content of a chlorogenic acid in solids of from 10 mass % to 70 mass %; a mass ratio of glucose/chlorogenic acid of from 0.1 to 0.9; a mass ratio of caffeine/chlorogenic acid of 0.05 or less; and a pH of from 1 to 5.

The present invention provides a method of producing a purified chlorogenic acid-containing composition, comprising:

a first step of bringing a chlorogenic acid-containing composition into contact with at least one of adsorbent selected from the group consisting of activated carbon, acid clay, and activated clay; and a second step of subjecting the chlorogenic acid-containing composition after the contact with the adsorbent to at least one selected from the group consisting of the following steps (A) and (B) under an acidic condition:

(A) a step of concentrating the chlorogenic acid-containing composition by 6 times or more; and (B) a step of adding glucose to the chlorogenic acid-containing composition.

DETAILED DESCRIPTION OF THE INVENTION

In Patent Document 1, a sensory evaluation is conducted by diluting a purified chlorogenic acid with water by 500 times. That is, the chlorogenic acid has a low concentration, and besides, a solution thereof has acidity or alkalinity in a more neutral region. Therefore, no investigation in Patent Document 1 is made into the taste and flavor of a chlorogenic acid at a high concentration under an acidic condition.

The inventors of the present invention investigated in detail the taste and flavor of a purified chlorogenic acid-containing composition having its chlorogenic acid enriched. As a result, they found a problem in that rough feeling on the tongue was felt in an aftertaste under an acidic condition. In addition, the unpleasant feeling on the tongue was not felt at all under a neutral condition, and hence found to be a novel problem that occurred specifically when the purified chlorogenic acid-containing composition having its chlorogenic acid enriched was under an acidic condition.

Therefore, the present invention relates to a purified chlorogenic acid-containing composition in which unpleasant feeling on the tongue under an acidic condition is improved, and a method of producing the same.

The inventors of the present invention made various investigations. As a result of investigations, they found that the unpleasant feeling on the tongue under an acidic condition can be improved by increasing the content of glucose and controlling a "glucose/chlorogenic acid" mass ratio within a specific range in a purified chlorogenic acid-containing composition having its chlorogenic acid enriched and containing less caffeine. In addition, they found that, when such purified chlorogenic acid-containing composition contains an excess of acetic acid in the composition balance of organic acids, its refreshing feeling of an aftertaste is impaired, whereas the refreshing feeling of an aftertaste can be improved by increasing the ratio of malic acid contained therein.

According to the present invention, it provides the purified chlorogenic acid-containing composition in which unpleasant feeling on the tongue under an acidic condition is improved. In addition, such purified chlorogenic acid-containing composition can be produced by a simple operation.

[Purified Chlorogenic Acid-Containing Composition]

A purified chlorogenic acid-containing composition of the present invention has a content of a chlorogenic acid in solids of from 10 mass % to 70 mass %. The content is preferably 20 mass % or more, more preferably 25 mass % or more, even more preferably 30 mass % or more, from the viewpoint of a physiological effect, and is preferably 60 mass % or less, more preferably 55 mass % or less, even more preferably 50 mass % or less, from the viewpoint of taste and flavor balance. Such content of the chlorogenic acid in solids falls within the range of preferably from 20 mass % to 60 mass %, more preferably from 25 mass % to 55 mass %, even more preferably from 30 mass % to 50 mass %. The term "chlorogenic acids" as used herein is a collective term for monocaffeoylquinic acids including 3-caffeoylquinic acid, 4-caffeoylquinic acid, and 5-caffeoylquinic acid, and monoferuloylquinic acids including 3-feruloylquinic acid, 4-feruloylquinic acid, and 5-feruloylquinic acid. The content of the chlorogenic acid is defined based on the total amount of the six kinds of chlorogenic acids. In the present invention, the purified chlorogenic acid-containing composition only needs to contain at least one of the six kinds of chlorogenic acids, but preferably contains all of the six kinds. In addition, the term "solid contents" as used herein refers to a residue obtained by drying a sample in an electric thermostat dryer at 105° C. for 3 hours to remove volatile substances.

The purified chlorogenic acid-containing composition of the present invention contains more glucose as compared to a generally contained amount, and contains the chlorogenic acid and glucose at a specific ratio. Specifically, a "glucose/chlorogenic acid" mass ratio is from 0.1 to 0.9. The "glucose/chlorogenic acid" mass ratio is preferably 0.11 or more, more preferably 0.12 or more, more preferably 0.13 or more, even more preferably 0.14 or more, from the viewpoint of the amelioration of unpleasant feeling on the tongue, and is preferably 0.8 or less, more preferably 0.5 or less, more preferably 0.4 or less, even more preferably 0.35 or less, from the viewpoints of a physiological effect and taste and flavor balance. Such "glucose/chlorogenic acid" mass ratio falls within the range of preferably from 0.11 to 0.8, more preferably from 0.12 to 0.5, more preferably from 0.13 to 0.4, even more preferably from 0.14 to 0.35.

The purified chlorogenic acid-containing composition of the present invention has a content of glucose in solids of preferably 4.5 mass % or more, more preferably 5.0 mass % or more, even more preferably 5.5 mass % or more, and of preferably 30 mass % or less, more preferably 20 mass % or less, even more preferably 15 mass % or less, from the viewpoint of the amelioration of unpleasant feeling on the tongue. Such content of glucose in solids falls within the range of preferably from 4.5 mass % to 30 mass %, more preferably from 5.0 mass % to 20 mass %, even more preferably from 5.5 mass % to 15 mass %. The glucose may be a single optically active substance or a mixture of optical isomers, and is preferably D-glucose. In addition, the glucose may be derived from a raw material or freshly added. The content of glucose is defined as the total amount of D-glucose and L-glucose.

In addition, the purified chlorogenic acid-containing composition of the present invention contains less caffeine as compared to a generally contained amount, and contains the chlorogenic acid and caffeine at a specific ratio. Specifically, a "caffeine/chlorogenic acid" mass ratio is 0.05 or less, and is preferably 0.04 or less, more preferably 0.03 or less, even more preferably 0.02 or less, from the viewpoint of taste and flavor balance. The "caffeine/chlorogenic acid" mass ratio may be 0.

The purified chlorogenic acid-containing composition of the present invention has a content of caffeine in solids of preferably 0.2 mass % or less, more preferably 0.15 mass % or less, even more preferably 0.1 mass % or less, from the viewpoint of taste and flavor balance. Such content of caffeine in solids may be 0 mass %. Herein, the concept that "the content of caffeine is 0 mass %" encompasses a case in which the content of caffeine is below the detection limit in the "analysis of caffeine" described in Examples to be described later.

The purified chlorogenic acid-containing composition of the present invention may contain malic acid and acetic acid at a specific ratio. Specifically, an "acetic acid/malic acid" mass ratio is preferably 0.3 or less, more preferably 0.2 or less, more preferably 0.1 or less, even more preferably 0.05 or less, from the viewpoint of an improvement in refreshing feeling of an aftertaste. The "acetic acid/malic acid" mass ratio may be 0.

The purified chlorogenic acid-containing composition of the present invention has a content of malic acid in solids of preferably 0.1 mass % or more, more preferably 0.5 mass % or more, even more preferably 1 mass % or more, from the viewpoint of an improvement in refreshing feeling of an aftertaste, and of preferably 5 mass % or less, more preferably 4 mass % or less, even more preferably 3 mass % or less, from the viewpoint of taste and flavor balance. Such content of malic acid in solids falls within the range of preferably from 0.1 mass % to 5 mass %, more preferably from 0.5 mass % to 4 mass %, even more preferably from 1 mass % to 3 mass %. The malic acid may be a single optically active substance or a mixture of optical isomers, and may be derived from a raw material or freshly added. The content of malic acid is defined as the total amount of D-malic acid and L-malic acid.

The purified chlorogenic acid-containing composition of the present invention has a content of acetic acid in solids of preferably 0.08 mass % or less, more preferably 0.06 mass % or less, even more preferably 0.05 mass % or less, from the viewpoint of an improvement in refreshing feeling of an aftertaste. Such content of acetic acid in solids may be 0 mass %. Herein, the concept that "the content of acetic acid is 0 mass %" encompasses a case in which the content of acetic acid is below the detection limit in the "analysis of acetic acid" described in Examples to be described later.

The purified chlorogenic acid-containing composition of the present invention may contain a lipid. The term "lipid" as used herein refers to what is measured by a method described in Examples to be described later. Examples thereof may include neutral lipids, such as triglycerides, sterols, and sterol esters, and phospholipids. The lipid is mainly derived from a blended component, and its amount is preferably reduced as compared to a generally contained amount. Specifically, the content of the lipid in solids of the purified chlorogenic acid-containing composition is preferably 0.3 mass % or less, more preferably 0.25 mass % or less, more preferably 0.2 mass % or less, even more preferably 0.1 mass % or less. Such content of the lipid in solids may be 0 mass %.

The pH (25° C.) of the purified chlorogenic acid-containing composition of the present invention is from 1 to 5. The pH is preferably 1.5 or more, more preferably 2.0 or more, even more preferably 2.5 or more, from the viewpoint of the amelioration of unpleasant feeling on the tongue, and is preferably 4.8 or less, more preferably 4.6 or less, even more preferably 4.5 or less, from the viewpoint of refreshing sourness. The pH falls within the range of preferably from 1.5 to 4.8, more preferably from 2.0 to 4.6, even more preferably from 2.5 to 4.5.

In the purified chlorogenic acid-containing composition of the present invention, unpleasant feeling on the tongue under an acidic condition is improved, and refreshing feeling of an aftertaste is excellent. Hence, it is useful as a raw material for the production of a food and drink or a supplement, in particular, a raw material for the production of a drink (preferably an acidic drink). A food and drink (preferably drink) having blended therein the purified chlorogenic acid-containing composition of the present invention may have the above-mentioned characteristics regarding the "glucose/chlorogenic acid" mass ratio, the "caffeine/chlorogenic acid" mass ratio, and the "acetic acid/malic acid" mass ratio.

The amount of the purified chlorogenic acid-containing composition to be blended into the drink may be appropriately selected, and for example, the purified chlorogenic acid-containing composition may be blended so that the drink may contain the chlorogenic acid at preferably from 0.001 mass % to 2.0 mass %, more preferably from 0.005 mass % to 1.0 mass %, even more preferably from 0.01 mass % to 0.5 mass %. In this case, the purified chlorogenic acid-containing composition may be diluted with water, another chlorogenic acid-containing composition, or the like so as to achieve a desired content of the chlorogenic acid. As the water, for example, tap water, distilled water, ion-exchanged water, or natural water may be appropriately selected and used. Of those, ion-exchanged water is preferred in terms of taste. The pH (25° C.) of the chlorogenic acid-containing drink is preferably from 1.0 to 5.0, more preferably from 1.5 to 4.5, even more preferably from 2.0 to 4.0.

Further, as desired, the chlorogenic acid-containing drink may contain one or two or more kinds of additives, such as an antioxidant, a sweetener (excluding glucose), an acidulant, an emulsifier, cocoa powder, an amino acid, a protein, a fragrance, a pigment, a fruit juice extract, fruit pieces, fruit powder, a vegetable extract, an herb, an inorganic salt, a pH adjuster, and a quality stabilizer. The content of any such additive may be appropriately selected within a range in which the object of the present invention is not impaired.

The drink may be a drink packaged in a container. The container is not particularly limited as long as the container is a general packaging container, and examples thereof include a molded container mainly formed of polyethylene terephthalate (so-called PET bottle), a metal can, a paper container composited with a metal foil or a plastic film, and a bottle.

In addition, the drink may be subjected to heat sterilization. A method for the heat sterilization is not particularly limited as long as the method complies with a condition specified by an applicable regulation (Food Sanitation Act in Japan). Examples thereof may include a retort sterilization method, a high-temperature short-time sterilization method (HTST method), and an ultrahigh-temperature sterilization method (UHT method). In addition, the method for the heat sterilization may be appropriately selected depending on the kind of the container. For example, when the drink, after being filled into a container, can be subjected to the heat sterilization together with the container, as in the case of a metal can, retort sterilization may be adopted. In addition, in the case of a container that cannot be subjected to retort sterilization, such as a PET bottle or a paper container, there may be adopted: aseptic filling, which involves subjecting a drink to heat sterilization in advance under sterilization conditions equivalent to those described above and filling the drink into a container having been subjected to sterilization treatment under an aseptic environment; hot-pack filling; or the like.

[Method of Producing Purified Chlorogenic Acid-Containing Composition]

The purified chlorogenic acid-containing composition of the present invention may be produced by an appropriate method as long as the produced composition has the above-mentioned characteristics. For example, the purified chlorogenic acid-containing composition of the present invention may be produced through steps including the following first step and second step. Each step is described in detail below.

<First Step>

The first step is a step of bringing a chlorogenic acid-containing composition into contact with at least one of adsorbent selected from the group consisting of activated carbon, acid clay, and activated clay.

(Chlorogenic Acid-Containing Composition)

The chlorogenic acid-containing composition to be used in the present invention is not particularly limited as long as the chlorogenic acid-containing composition contains a chlorogenic acid, and an example thereof may be an extract of a plant containing a chlorogenic acid. Examples of the plant containing a chlorogenic acid include sunflower seeds, unripe apples, coffee beans, simon leaves, pinaceous cones, pinaceous seed hulls, sugarcane, nandina leaves, burdock, eggplant skins, ume fruit, coltsfoot, and vitaceous plants. Of those, coffee beans are preferred as the plant containing a chlorogenic acid from the standpoint of the content of the chlorogenic acid.

Coffee beans to be used are preferably at least one selected from the group consisting of green coffee beans, decaffeinated green coffee beans, roasted coffee beans having an L value of 45 or more, and decaffeinated roasted coffee beans having an L value of 25 or more from the standpoint of the content of the chlorogenic acid. As used herein, the term "decaffeinated green coffee beans" refers to coffee beans obtained by subjecting green coffee beans to decaffeination treatment, the term "roasted coffee beans having an L value of 45 or more" refers to coffee beans obtained by subjecting green coffee beans to roasting treatment so as to have an L value of 45 or more, and the term "decaffeinated roasted coffee beans having an L value of 25 or more" refers to coffee beans obtained by subjecting decaffeinated green coffee beans to roasting treatment so as to have an L value of 25 or more. Of those, as the coffee beans, green coffee beans are preferred from the standpoint of the content of the chlorogenic acid.

The bean species of the coffee beans may be, for example, any one of *Arabica, Robusta, Liberica,* and *Arabusta*. In addition, the producing region of the coffee beans is not particularly limited, and examples thereof include Brazil, Colombia, Tanzania, Mocha, Kilimanjaro, Mandheling, Blue Mountain, Guatemala, and Vietnam.

As the roasted coffee beans, ones having an L value of 45 or more are suitably used, and the L value is preferably 50 or more, more preferably 53 or more, even more preferably 55 or more, from the standpoint of the content of the chlorogenic acid, and is preferably less than 65, more preferably 60 or less, even more preferably 58 or less, from the viewpoint of taste and flavor. The L value of the roasted coffee beans falls within the range of preferably 50 or more and less than 65, more preferably 53 or more and less than 65, more preferably from 55 to 60, even more preferably from 55 to 58.

Meanwhile, as the decaffeinated roasted coffee beans, ones having an L value of 25 or more are suitably used, and the L value is preferably 30 or more, more preferably 33 or more, from the standpoint of the content of the chlorogenic acid, and is preferably less than 50, more preferably 45 or less, even more preferably 40 or less, from the viewpoint of taste and flavor. The L value of the decaffeinated roasted coffee beans falls within the range of preferably 25 or more and less than 50, more preferably from 30 to 45, even more preferably from 33 to 40.

The term "L value" as used herein refers to a value as determined by measuring the lightness of the roasted coffee beans with a colorimeter under the assumption that black has an L value of 0 and white has an L value of 100. A roasting method and roasting conditions are not particularly limited, and a known method and conditions may be adopted.

As a method of decaffeinating the green coffee beans, a known method, such as a Swiss Water method, a supercritical carbon dioxide extraction method, or an organic solvent extraction method, may be adopted. Of those, a Swiss Water method or a supercritical carbon dioxide extraction method is preferred.

In addition, with regard to their particle size, the coffee beans may be unground (whole) coffee beans, ground coffee beans, or a mixture thereof. Of those, unground (whole) coffee beans are preferred from the viewpoint of a reduction in lipid content of the purified chlorogenic acid-containing composition to be obtained by this production method.

The average particle size of the ground coffee beans is preferably 0.3 mm or more, more preferably 0.5 mm or more, even more preferably 1.0 mm or more, from the viewpoint of a reduction in lipid content of the purified chlorogenic acid-containing composition to be obtained by this production method, and is preferably 7.5 mm or less, more preferably 7.0 mm or less, even more preferably 6.5 mm or less, from the viewpoint of an increase in recovery rate of the chlorogenic acid. Such average particle size falls within the range of preferably from 0.3 mm to 7.5 mm, more preferably from 0.5 mm to 7.0 mm, even more preferably from 1.0 mm to 6.5 mm. The term "average particle size" as used herein refers to one measured by a measurement method described in Examples to be described later.

A method of grinding the coffee beans is not particularly limited, and a known method and apparatus may be used. Examples of the grinding apparatus may include a cutter mill, a hammer mill, a jet mill, an impact mill, and a Wiley mill. Examples of the cutter mill include a roll grinder, a flat cutter, a conical cutter, and a grade grinder. In addition, the ground coffee beans may be classified so as to have an average particle size in the above-mentioned range through the use of, for example, a Tyler standard sieve, an ASTM standard sieve, or a JIS standard sieve.

The coffee beans may be used alone or in combination thereof. When two or more kinds of coffee beans are used, not only coffee beans different in bean species or producing region, but also coffee beans different in degree of roasting or particle size may be appropriately selected and used in any combination. When coffee beans different in degree of roasting are used, the coffee beans are preferably used in such an appropriate combination that the average of their L values falls within the above-mentioned range. The average of the L values is determined as a sum of values each obtained by multiplying an L value of roasted coffee beans by a content mass ratio of the roasted coffee beans.

As a method of extracting the plant containing a chlorogenic acid, there may be given, for example, known methods such as column extraction and batch extraction. Of those, column extraction is preferred from the viewpoint of a reduction in turbidity. Extraction conditions are not particularly limited, and known conditions may be appropriately selected.

The chlorogenic acid-containing composition to be brought into contact with the adsorbent in the present invention has solids concentration of preferably 4.7 mass % or less, more preferably 4.5 mass % or less, more preferably 4.0 mass % or less, even more preferably 3.5 mass % or less, from the viewpoint of an improvement in refreshing feeling of an aftertaste. The lower limit value of such solid contents concentration may be appropriately selected, and is preferably 0.1 mass % or more, more preferably 1.0 mass % or more, even more preferably 1.1 mass % or more, from the viewpoint of production efficiency. Such solid contents concentration falls within the range of preferably from 0.1 mass % to 4.7 mass %, more preferably from 1.0 mass % to 4.5 mass %, more preferably from 1.1 mass % to 4.0 mass %, even more preferably from 1.1 mass % to 3.5 mass %. For example, in the case where the extract solution is continuously discharged and solids concentration of the discharged extract solution varies as in the column extraction, it is preferred that solids concentration of the whole amount of the extract solution discharged fall within the above-mentioned range. With such low concentration, each component contained in the chlorogenic acid-containing composition to be brought into contact with the adsorbent in the present invention has enhanced adsorption selectivity for the adsorbent. Presumably as a result of this, the "acetic acid/malic acid" mass ratio in the purified chlorogenic acid-containing composition obtained by the present invention falls within the above-mentioned range.

In addition, the chlorogenic acid-containing composition to be brought into contact with the adsorbent in the present invention has a content of the chlorogenic acid in solids of preferably 1 mass % or more, more preferably 5 mass % or more, even more preferably 10 mass % or more, and of preferably 70 mass % or less, more preferably 60 mass % or less, even more preferably 50 mass % or less, from the viewpoint of production efficiency. Such content of the chlorogenic acid in solids falls within the range of preferably from 1 mass % to 70 mass %, more preferably from 5 mass % to 60 mass %, even more preferably from 10 mass % to 50 mass %. In order to achieve such solid contents concentration and content of the chlorogenic acid in solids, for example, the obtained extract may be diluted or concentrated. A known method to be described later may be adopted as a concentration method, and concentration conditions may be appropriately selected depending on the concentration method.

(Adsorbent)

At least one selected from the group consisting of activated carbon, acid clay, and activated clay is used as the adsorbent. Of those, activated carbon is preferred.

The usage amount of the adsorbent with respect to solids of the chlorogenic acid-containing composition is preferably 50 mass % or more, more preferably 80 mass % or more, even more preferably 150 mass % or more, from the viewpoint of a reduction in caffeine, and is preferably 400 mass % or less, more preferably 370 mass % or less, even more preferably 350 mass % or less, from the viewpoint of an increase in recovery rate of the chlorogenic acid. The usage amount of the adsorbent falls within the range of preferably from 50 mass % to 400 mass %, more preferably from 80 mass % to 370 mass %, even more preferably from 150 mass % to 350 mass %, with respect to solids of the chlorogenic acid-containing composition.

As a method for the contact with the adsorbent, there may be given, for example, a batchwise method and a continuous method. Of those, a continuous method involving continuously passing the chlorogenic acid-containing composition through a column filled with the adsorbent is preferred from the viewpoint of production efficiency. In the case of the continuous method, the chlorogenic acid-containing composition may be supplied from the lower part of the column toward the upper part thereof (upflow), or may be supplied from the upper part toward the lower part (downflow), and the supply direction may be appropriately selected.

In the case of the continuous method, a space velocity (SV) with respect to the mass of the adsorbent is preferably 0.1 $[h^{-1}]$ or more, more preferably 1.0 $[h^{-1}]$ or more, even more preferably 5.0 $[h^{-1}]$ or more, and is preferably 20 $[h^{-1}]$ or less, more preferably 15 $[h^{-1}]$ or less, even more preferably 10 $[h^{-1}]$ or less. Such space velocity (SV) falls within the range of preferably from 0.1 $[h^{-1}]$ to 20 $[h^{-1}]$, more preferably from 1.0 $[h^{-1}]$ to 15 $[h^{-1}]$, even more preferably from 5.0 $[h^{-1}]$ to 10 $[h^{-1}]$.

After the contact with the adsorbent, the liquid having been treated with the adsorbent may be subjected to solid-liquid separation. The solid-liquid separation is not particularly limited as long as the solid-liquid separation is usually used in the field of food industry, and examples thereof include paper filtration, centrifugal separation, and membrane filtration. One thereof may be carried out, or two or more kinds thereof may be carried out in combination.

<Second Step>

The second step is a step of subjecting the chlorogenic acid-containing composition after the treatment with the adsorbent to at least one selected from the group consisting of the step (A) and the step (B) under an acidic condition.

(Acidic Condition)

The acidic condition is not particularly limited as long as a pH (25° C.) is less than 7.0. The pH is preferably 1.0 or more, more preferably 2.0 or more, even more preferably 2.5 or more, from the viewpoint of the amelioration of unpleasant feeling on the tongue, and is preferably 5.0 or less, more preferably 4.5 or less, even more preferably 4.0 or less, from the viewpoint of the impartment of refreshing sourness. Such pH falls within the range of preferably from 1.0 to 5.0, more preferably from 2.0 to 4.5, even more preferably from 2.5 to 4.0.

As a method of making the acidic condition, there may be given, for example, addition of an acid, electrodialysis, and contact with a cation-exchange resin. Of those, contact with a cation-exchange resin is preferred from the viewpoint of production efficiency. When the pH of the chlorogenic acid-containing composition after the treatment with the adsorbent falls within the above-mentioned range, the chlorogenic acid-containing composition may be used as it is without pH adjustment.

Any of an organic acid, an inorganic acid, and salts thereof may be used as the acid. Examples thereof include: organic acids, such as citric acid, lactic acid, tartaric acid, succinic acid, malic acid, and ascorbic acid; inorganic acids, such as phosphoric acid and hydrochloric acid; and salts thereof. Examples of the salts may include salts with alkali metals, such as sodium. The acid may be added to the chlorogenic acid-containing composition as it is or in the form of an aqueous solution having dissolved therein the acid. The addition amount of the acid only needs to be appropriately set so as to achieve a desired pH depending on the kind of the acid.

For the electrodialysis, an apparatus in which pluralities of cation exchangers and anion exchangers are alternately arranged between an anode and a cathode from the cathode side may be used.

Examples of the cation-exchange resin include cation-exchange resins having a sulfonic acid group, a carboxyl group, and a phosphoric acid group. Of those, a cation-exchange resin having a sulfonic acid group is preferred. As a commercially available product thereof, there may be given, for example, Amberlite 200CT, Amberlite IR120B, Amberlite IR124, and Amberlite IR118 (all of which are available from Organo Corporation (supplier: Rohm and Haas Company, US)), and DIAION SK1B, DIAION SK1BH, DIAION SK102, DIAION PK208, and DIAION PK212 (all of which are manufactured by Mitsubishi Chemical Corporation).

As a method for the contact with the cation-exchange resin, there may be given, for example, a batchwise method and a continuous method. Of those, a continuous method involving continuously passing the chlorogenic acid-containing composition through a column filled with the cation-exchange resin is preferred from the viewpoint of production efficiency. Feeding conditions for the chlorogenic acid-containing composition may be appropriately set, and for example, a space velocity (SV) is preferably from 0.1 $[hr^{-1}]$ to 50 $[hr^{-1}]$, more preferably from 0.1 $[hr^{-1}]$ to 10 $[hr^{-1}]$, more preferably from 0.2 $[hr^{-1}]$ to 8 $[hr^{-1}]$, even more preferably from 0.5 $[hr^{-1}]$ to 5 $[hr^{-1}]$.

(Step A)

The step (A) is a step of concentrating the chlorogenic acid-containing composition by 6 times or more, after the treatment with the adsorbent.

As a concentration method, there are given, for example, a normal-pressure concentration method involving vaporizing a solvent at normal pressure, a reduced-pressure concentration method involving vaporizing a solvent under reduced pressure, and a membrane concentration method involving removing a solvent by membrane separation. Of those, a reduced-pressure concentration method is preferred from the viewpoints of production efficiency and quality maintenance. In order to achieve the reduced pressure, for example, a water ring pump, a water jet pump, or a vacuum pump may be used. In addition, a temperature at the time of the concentrating is preferably from 20° C. to 70° C., more preferably from 25° C. to 65° C., even more preferably from 30° C. to 60° C.

The concentration factor of the chlorogenic acid-containing composition after the treatment with the adsorbent is preferably 6.5 times or more, more preferably 7.5 times or more, even more preferably 8.5 times or more, from the viewpoint of the amelioration of unpleasant feeling on the tongue. The upper limit value of the concentration factor is preferably 100 times or less, more preferably 80 times or less, even more preferably 60 times or less, from the viewpoint of production efficiency. Such concentration factor falls within the range of preferably from 6.5 times to 100 times, more preferably from 7.5 times to 80 times, even more preferably from 8.5 times to 60 times.

The content of the chlorogenic acid in solids of the chlorogenic acid-containing composition after the concentrating is preferably 10 mass % or more, more preferably 20 mass % or more, more preferably 25 mass % or more, even more preferably 30 mass % or more. The upper limit value of such content of the chlorogenic acid in solids is preferably 70 mass % or less, more preferably 60 mass % or less, more preferably 55 mass % or less, even more preferably 50 mass % or less, from the viewpoint of production efficiency. Such content of the chlorogenic acid in solids falls within the range of preferably from 10 mass % to 70 mass %, more preferably from 20 mass % to 60 mass %, more preferably from 25 mass % to 55 mass %, even more preferably from 30 mass % to 50 mass %.

(Step B)

The step (B) is a step of adding glucose to the chlorogenic acid-containing composition after the treatment with the adsorbent.

The addition amount of glucose is not particularly limited as long as the "glucose/chlorogenic acid" mass ratio falls within the range of from 0.1 to 0.9, and the addition amount may be appropriately selected. In addition, when the "glucose/chlorogenic acid" mass ratio falls within the above-mentioned range, the step (B) does not necessarily need to be performed, but the chlorogenic acid-containing composition may be subjected to the step (B) to be adjusted to the above-mentioned suitable "glucose/chlorogenic acid" mass ratio. A commercially available product or a commercially available reagent may be used as the glucose.

The step (A) and the step (B) may each be appropriately selected depending on the physical properties of the chlorogenic acid-containing composition after the treatment with the adsorbent. From the viewpoint of the amelioration of unpleasant feeling on the tongue, the chlorogenic acid-containing composition is preferably subjected to the step (A), or both the step (A) and the step (B). When both the steps (A) and (B) are performed, their order is not particularly limited.

The purified chlorogenic acid-containing composition of the present invention may be obtained as described above. The purified chlorogenic acid-containing composition may be in any of various forms, such as a liquid, a slurry, a semisolid, and a solid. In addition, the purified chlorogenic acid-containing composition may be further concentrated in order to increase solids concentration. As a concentration method, the same methods as those described above are given. Further, when a solid is preferred as the product form of the purified chlorogenic acid-containing composition, the purified chlorogenic acid-containing composition may be dried by a known method, such as spray drying or freeze drying.

The present invention further discloses the following purified chlorogenic acid-containing composition and method of producing the same, regarding the above-mentioned embodiment.

<1A-1>

A purified chlorogenic acid-containing composition, having:

a content of a chlorogenic acid in solids of from 10 mass % to 70 mass %;

a mass ratio of glucose/chlorogenic acid of from 0.1 to 0.9;

a mass ratio of caffeine/chlorogenic acid of 0.05 or less; and a pH of from 1 to 5.

<1A-2>

The purified chlorogenic acid-containing composition according to the above-mentioned item <1A-1>, wherein the content of the chlorogenic acid in solids is preferably from 20 mass % to 60 mass %, more preferably from 25 mass % to 55 mass %, even more preferably from 30 mass % to 50 mass %.

<1A-3>

The purified chlorogenic acid-containing composition according to the above-mentioned item <1A-1> or <1A-2>, wherein the purified chlorogenic acid-containing composition has a content of glucose in solids of preferably from 4.5 mass % to 30 mass %, more preferably from 5.0 mass % to 20 mass %, even more preferably from 5.5 mass % to 15 mass %.

<1A-4>

The purified chlorogenic acid-containing composition according to anyone of the above-mentioned items <1A-1> to <1A-3>, wherein the purified chlorogenic acid-containing composition has a content of caffeine in solids of preferably 0.2 mass % or less, more preferably 0.15 mass % or less, even more preferably 0.1 mass % or less, and the content of caffeine in solids may be 0 mass %.

<1A-5>

The purified chlorogenic acid-containing composition according to anyone of the above-mentioned items <1A-1> to <1A-4>, wherein the purified chlorogenic acid-containing composition has a content of malic acid in solids of preferably from 0.1 mass % to 5 mass %, more preferably from 0.5 mass % to 4 mass %, even more preferably from 1 mass % to 3 mass %.

<1A-6>

The purified chlorogenic acid-containing composition according to any one of the above-mentioned items <1A-1> to <1A-5>, wherein the purified chlorogenic acid-containing composition has a content of acetic acid in solids of preferably 0.08 mass % or less, more preferably 0.06 mass % or less, even more preferably 0.05 mass % or less, and the content of acetic acid in solids may be 0 mass %.

<1A-7>

The purified chlorogenic acid-containing composition according to any one of the above-mentioned items <1A-1> to <1A-6>, wherein the purified chlorogenic acid-containing composition has a content of a lipid in solids of preferably 0.3 mass % or less, more preferably 0.25 mass % or less, more preferably 0.2 mass % or less, even more preferably 0.1 mass % or less, and the content of the lipid in solids may be 0 mass %.

<1A-8>

The purified chlorogenic acid-containing composition according to any one of the above-mentioned items <1A-1> to <1A-7>, wherein the pH is preferably from 1.5 to 4.8, more preferably from 2.0 to 4.6, even more preferably from 2.5 to 4.5.

<1A-9>

The purified chlorogenic acid-containing composition according to any one of the above-mentioned items <1A-1> to <1A-8>, wherein the mass ratio of glucose/chlorogenic acid is preferably from 0.11 to 0.8, more preferably from 0.13 to 0.5, more preferably from 0.14 to 0.4, even more preferably from 0.15 to 0.4, and may be preferably from 0.12 to 0.5, more preferably from 0.13 to 0.4, even more preferably from 0.14 to 0.35.

<1A-10>

The purified chlorogenic acid-containing composition according to any one of the above-mentioned items <1A-1> to <1A-9>, wherein the mass ratio of caffeine/chlorogenic acid is preferably 0.04 or less, more preferably 0.03 or less, even more preferably 0.02 or less, and may be 0.

<1A-11>

The purified chlorogenic acid-containing composition according to any one of the above-mentioned items <1-1> to <1-10>, wherein the purified chlorogenic acid-containing composition has a mass ratio of acetic acid/malic acid of preferably 0.3 or less, more preferably 0.2 or less, more preferably 0.1 or less, even more preferably 0.05 or less, and the mass ratio of acetic acid/malic acid may be 0.

<1A-12>

The purified chlorogenic acid-containing composition according to any one of the above-mentioned items <1A-1> to <1A-11>, wherein the chlorogenic acid comprises preferably at least one selected from the group consisting of 3-caffeoylquinic acid, 4-caffeoylquinic acid, 5-caffeoylquinic acid, 3-feruloylquinic acid, 4-feruloylquinic acid, and 5-feruloylquinic acid, more preferably all of the six kinds.

<1B-1>

A purified chlorogenic acid-containing composition, having:

a content of a chlorogenic acid in solids of from 30 mass % to 50 mass %;

a content of a lipid in solids of 0.1 mass % or less;

a mass ratio of glucose/chlorogenic acid of from 0.1 to 0.9;

a mass ratio of caffeine/chlorogenic acid of 0.05 or less; and a pH of from 1.0 to 5.0.

<1B-2>

The purified chlorogenic acid-containing composition according to the above-mentioned item <1B-1>, wherein the mass ratio of glucose/chlorogenic acid is preferably from 0.11 to 0.8, more preferably from 0.12 to 0.5, more preferably from 0.13 to 0.4, even more preferably from 0.14 to 0.35.

<1B-3>

The purified chlorogenic acid-containing composition according to the above-mentioned item <1B-1> or <1B-2>, wherein the mass ratio of caffeine/chlorogenic acid is preferably 0.04 or less, more preferably 0.03 or less, even more preferably 0.02 or less, and may be 0.

<1B-4>
The purified chlorogenic acid-containing composition according to any one of the above-mentioned items <1B-1> to <1B-3>, wherein the pH is preferably from 1.5 to 4.8, more preferably from 2.0 to 4.6, even more preferably from 2.5 to 4.5.

<1B-5>
The purified chlorogenic acid-containing composition according to any one of the above-mentioned items <1B-1> to <1B-4>, wherein the purified chlorogenic acid-containing composition has an mass ratio of acetic acid/malic acid of preferably 0.3 or less, more preferably 0.2 or less, more preferably 0.1 or less, even more preferably 0.05 or less, and the mass ratio of acetic acid/malic acid may be 0.

<1B-6>
The purified chlorogenic acid-containing composition according to any one of the above-mentioned items <1B-1> to <1B-5>, wherein the chlorogenic acid comprises preferably at least one selected from the group consisting of 3-caffeoylquinic acid, 4-caffeoylquinic acid, 5-caffeoylquinic acid, 3-feruloylquinic acid, 4-feruloylquinic acid, and 5-feruloylquinic acid, more preferably all of the six kinds.

<2-1>
A method of producing a purified chlorogenic acid-containing composition, comprising:
a first step of bringing a chlorogenic acid-containing composition into contact with at least one of adsorbent selected from the group consisting of activated carbon, acid clay, and activated clay; and
a second step of subjecting the chlorogenic acid-containing composition after the contact with the adsorbent to at least one selected from the group consisting of the following steps (A) and (B) under an acidic condition:
  (A) a step of concentrating the chlorogenic acid-containing composition by 6 times or more; and
  (B) a step of adding glucose to the chlorogenic acid-containing composition.

<2-2>
The method of producing a purified chlorogenic acid-containing composition according to the above-mentioned item <2-1>, wherein the chlorogenic acid-containing composition preferably comprises an extract of coffee beans.

<2-3>
The method of producing a purified chlorogenic acid-containing composition according to the above-mentioned item <2-2>, wherein the coffee beans preferably comprise at least one selected from the group consisting of green coffee beans, decaffeinated green coffee beans, roasted coffee beans having an L value of 45 or more, and decaffeinated roasted coffee beans having an L value of 25 or more.

<2-4>
The method of producing a purified chlorogenic acid-containing composition according to the above-mentioned item <2-2> or <2-3>, wherein, with regard to their particle size, the coffee beans comprise preferably unground (whole) coffee beans, ground coffee beans, or a mixture thereof, more preferably unground (whole) coffee beans.

<2-5>
The method of producing a purified chlorogenic acid-containing composition according to the above-mentioned item <2-4>, wherein the ground coffee beans have an average particle size of preferably from 0.3 mm to 7.5 mm, more preferably from 0.5 mm to 7 mm, even more preferably from 1.0 mm to 6.5 mm.

<2-6>
The method of producing a purified chlorogenic acid-containing composition according to any one of the above-mentioned items <2-2> to <2-5>, wherein an extraction method for the extract of coffee beans comprises preferably column extraction or batch extraction, more preferably column extraction.

<2-7>
The method of producing a purified chlorogenic acid-containing composition according to any one of the above-mentioned items <2-1> to <2-6>, wherein the chlorogenic acid-containing composition in the first step has solids concentration of preferably from 0.1 mass % to 4.7 mass %, more preferably from 1.0 mass % to 4.5 mass %, more preferably from 1.1 mass % to 4.0 mass %, even more preferably from 1.1 mass % to 3.5 mass %.

<2-8>
The method of producing a purified chlorogenic acid-containing composition according to any one of the above-mentioned items <2-1> to <2-7>, wherein the chlorogenic acid-containing composition in the first step has a content of a chlorogenic acid in solids of preferably from 1 mass % to 70 mass %, more preferably from 5 mass % to 60 mass %, even more preferably from 10 mass % to 50 mass %.

<2-9>
The method of producing a purified chlorogenic acid-containing composition according to any one of the above-mentioned items <2-1> to <2-8>, wherein the acidic condition comprises a pH of preferably from 1.0 to 5.0, more preferably from 2.0 to 4.5, even more preferably from 2.5 to 4.0.

<2-10>
The method of producing a purified chlorogenic acid-containing composition according to any one of the above-mentioned items <2-1> to <2-9>, wherein a method of making the acidic condition comprises addition of an acid, electrodialysis, or contact with a cation-exchange resin, more preferably contact with a cation-exchange resin.

<2-11>
The method of producing a purified chlorogenic acid-containing composition according to the above-mentioned item <2-10>, wherein the acid comprises preferably one or two or more kinds selected from the group consisting of organic acids, inorganic acids, and salts thereof (e.g., salts with alkali metals, such as sodium), more preferably one or two or more kinds selected from the group consisting of citric acid, lactic acid, tartaric acid, succinic acid, malic acid, ascorbic acid, phosphoric acid, hydrochloric acid, and salts thereof.

<2-12>
The method of producing a purified chlorogenic acid-containing composition according to the above-mentioned item <2-10>, wherein the cation-exchange resin comprises preferably a cation-exchange resin having a sulfonic acid group, a carboxyl group, or a phosphoric acid group, more preferably a cation-exchange resin having a sulfonic acid group.

<2-13>
The method of producing a purified chlorogenic acid-containing composition according to any one of the above-mentioned items <2-1> to <2-12>, wherein a concentration method in the step (A) comprises preferably a normal-pressure concentration method, a reduced-pressure concentration method, or a membrane concentration method, more preferably a reduced-pressure concentration method.

<2-14>
The method of producing a purified chlorogenic acid-containing composition according to any one of the above-mentioned items <2-1> to <2-13>, wherein a concentration temperature in the step (A) is preferably from 20° C. to 70° C., more preferably from 25° C. to 65° C., even more preferably from 30° C. to 60° C.

<2-15>

The method of producing a purified chlorogenic acid-containing composition according to any one of the above-mentioned items <2-1> to <2-14>, wherein a concentration factor in the step (A) is preferably from 6.5 times to 100 times, more preferably from 7.5 times to 80 times, even more preferably from 8.5 times to 60 times.

<2-16>

The method of producing a purified chlorogenic acid-containing composition according to any one of the above-mentioned items <2-1> to <2-15>, wherein the chlorogenic acid-containing composition after the concentrating has a content of a chlorogenic acid in solids of preferably from 10 mass % to 70 mass %, more preferably from 20 mass % to 60 mass %, more preferably from 25 mass % to 55 mass %, even more preferably from 30 mass % to 50 mass %.

<2-17>

The method of producing a purified chlorogenic acid-containing composition according to any one of the above-mentioned items <2-1> to <2-16>, wherein the second step preferably comprises subjecting the chlorogenic acid-containing composition to the step (A), or both the step (A) and the step (B).

<2-18>

The method of producing a purified chlorogenic acid-containing composition according to any one of the above-mentioned items <2-1> to <2-17>, further comprising, after the second step, a step of concentrating or drying the chlorogenic acid-containing composition.

<2-19>

The method of producing a purified chlorogenic acid-containing composition according to any one of the above-mentioned items <2-1> to <2-18>, wherein the purified chlorogenic acid-containing composition is preferably in a liquid, slurry, semisolid, or solid form.

EXAMPLES

1. Analysis of Chlorogenic Acid (CGA) and Caffeine (Cat) (Analyzer)

An UPLC (manufactured by Nihon Waters K.K.) was used. The model numbers of component units in the analyzer are as follows:
Apparatus: Waters ACQUITY UPLC
Column: ACQUITY UPLC TM C18, 2.1×100 nm, 1.7 μm
Detector: photodiode array detector (PDA)
(Analysis Conditions)
Sample injection volume: 10 μL
Flow rate: 1.0 mL/min
Ultraviolet absorption spectrophotometer detection wavelengths: 325 nm (chlorogenic acid) and 270 nm (caffeine)
Eluent A: A solution of acetonitrile diluted with water to an acetonitrile concentration of 5 (V/V) %, the solution containing 0.05 M acetic acid, 0.1 mM 1-hydroxyethane-1,1-diphosphonic acid, and 10 mM sodium acetate
Eluent B: Acetonitrile
Concentration Gradient Conditions (vol %)

| Time | Eluent A | Eluent B |
| --- | --- | --- |
| 0.0 min | 100% | 0% |
| 2.5 min | 100% | 0% |
| 3.5 min | 95% | 5% |
| 5.0 min | 95% | 5% |
| 6.0 min | 92% | 8% |
| 16.0 min | 92% | 8% |
| 16.5 min | 10% | 90% |
| 19.0 min | 100% | 0% |
| 22.0 min | 100% | 0% |

(1) Retention Time of Chlorogenic Acid (CGA)
3-Caffeoylquinic acid (3-CQA): 1.3 min
5-Caffeoylquinic acid (5-CQA): 2.1 min
4-Caffeoylquinic acid (4-CQA): 2.9 min
3-Feruloylquinic acid (3-FQA): 3.3 min
5-Feruloylquinic acid (5-FQA): 5.0 min
4-Feruloylquinic acid (4-FQA): 5.4 min
5-CQA was used as a standard substance to determine the content (mass %) of the chlorogenic acid based on the area % determined in the foregoing.

(2) Retention Time of Caffeine (Caf)
Caffeine: 4.8 min
Reagent caffeine was used as a standard substance to determine the content (mass %) of caffeine based on the area % determined in the foregoing.

2. Analysis of Glucose

A sample was neutralized with a 10% sodium hydroxide aqueous solution, and then ultrasonicated for 30 minutes. Next, the resultant was diluted in a measuring cylinder with ion-exchanged water to adjust the volume properly, filtered, and then analyzed with a high performance liquid chromatograph.
(Analyzer)
Model: LC-20AD (manufactured by Shimadzu Corporation)
Detector: fluorescence spectrophotometer (manufactured by Shimadzu Corporation)
Column: Wakosil 5NH2 φ4.6 mm×250 mm (manufactured by Wako Pure Chemical Industries, Ltd.)
Column temperature: 25° C.
Mobile phase: acetonitrile:water=75:25
Flow rate: 1 mL/min
Injection volume: 2 μL 3. Analysis of Malic Acid and Acetic Acid A sample and 0.5% perchloric acid were mixed with each other, and the mixture was diluted in a measuring cylinder with ion-exchanged water, filtered, and then analyzed with a high performance liquid chromatograph.
(Analyzer)
Model: LC-20AD (manufactured by Shimadzu Corporation)
Detector: electric conductivity detector CDD-10AVP (manufactured by Shimadzu Corporation)
Column: Shim-pack SCR-102H×2 φ8 mm×300 mm (manufactured by Hitachi Chemical Company, Ltd.)
Column temperature: 45° C.
Mobile phase: 5 mmol/L p-toluenesulfonic acid aqueous solution
Reaction solution: An aqueous solution obtained by diluting p-toluenesulfonic acid with water to a p-toluenesulfonic acid concentration of 5 mmol/L, the aqueous solution containing 20 mmol/L Bis-Tris and 0.1 mmol/L EDTA
Flow rate: 0.8 mL/min for the mobile phase, 0.8 mL/min for the reaction solution
Injection volume: 10 μL 4. Analysis of Lipid 10 g of a sample was collected, mixed with 100 mL of water, and dissolved with 20 mL of a 7% copper sulfate solution and 10 mL of a 3% sodium hydroxide solution. The solution was filtered through pleated filter paper, and the residue was washed with 100 mL of water. The pleated filter paper was dried, followed by treatment with diethyl ether for 16 hours or more through the use of a Soxhlet extractor. After that, diethyl ether was removed by evaporation with a water bath, and the residue was dried in a constant-temperature dryer at 105° C. for about 1 hour, allowed to cool in a desiccator, and then weighed.

5. Analysis of pH

Measurement was performed at a temperature adjusted to 25° C. using a pH meter (HORIBA Compact pH Meter, manufactured by Horiba, Ltd.).

6. Measurement of L Value of Roasted Coffee Beans

A sample was subjected to measurement using a colorimeter (manufactured by Nippon Denshoku Industries Co., Ltd., Spectrophotometer SE2000).

7. Measurement of Average Particle Size of Ground Coffee Beans

Ten ground coffee beans were randomly taken, each of the beans was measured for its long diameter, short diameter, and intermediate diameter with a vernier caliper, and the average of the measured values was defined as an average particle size. As used herein, the term "long diameter" refers to the length of the longest portion in an observation surface of a ground coffee bean, the term "short diameter" refers to the length of the longest portion in the direction perpendicular to the long diameter, and the term "intermediate diameter" refers to the length of the longest portion in the vertical direction of the observation surface. However, when such value was 2 mm or less, the "average particle size" was determined as a particle size corresponding to 50% ($d_{50}$) in a cumulative particle size distribution curve on a volume basis obtained by dry measurement with a laser diffraction/scattering particle size distribution analyzer (LS13 320, manufactured by Beckman Coulter) utilizing the dependence of a diffracted/scattered light intensity pattern on the size of a particle.

8. Sensory Evaluation

Purified chlorogenic acid-containing compositions obtained in Examples and Comparative Examples were each diluted with ion-exchanged water so as to have a chlorogenic acid concentration of 0.3 mass % to prepare a drink. Then, the drink was drunk by one expert panelist, and evaluated for "rough feeling on the tongue remaining after drinking" and "refreshing sourness" by the following evaluation criteria.

Evaluation Criteria for "Rough Feeling on the Tongue Remaining After Drinking"

Evaluation was performed with the score for the rough feeling on the tongue remaining after drinking of Comparative Example 1 being defined as "0" and the score for the rough feeling on the tongue remaining after drinking of Reference Example 1 being defined as "+2". Specific evaluation criteria are as described below.

+2: Having little roughness to be felt, comparable to Reference Example 1

+1: Having weaker roughness than Comparative Example 1

0: Rough comparably to Comparative Example 1

−1: Rougher than Comparative Example 1

Evaluation Criteria for "Refreshing Sourness"

Evaluation was performed with the score for the sourness of Example 8 being defined as "0". Specific evaluation criteria are as described below.

+2: Having strong refreshing sourness as compared to Example 8

+1: Having slightly strong refreshing sourness as compared to Example 8

0: Comparable to Example 8

−1: Having weak refreshing sourness as compared to Example 8

Comparative Example 1

8.5 kg of unground green robusta coffee beans were treated in an autoclave at 110° C. for 10 minutes to provide steamed beans. The resultant steamed beans were charged into a 40 L extraction column. Next, 3 parts by mass of hot water at 80° C. was supplied to the extraction column from a supply valve in an upper part of the extraction column at a feeding rate of SV=2 [hr$^{-1}$] to charge the extraction column. Next, hot water at 80° C. was supplied from the upper part of the extraction column under the conditions of a feeding rate of SV=2 [hr$^{-1}$] and a bed volume (BV) of 15 (w/w), and simultaneously, an extract solution was obtained by being discharged from a lower part of the extraction column. The whole amount of the extract solution obtained had solids concentration of 1.1% and a content of a chlorogenic acid in solids of 30 mass %.

The extract solution discharged from the lower part of the extraction column was continuously supplied to an activated carbon column having a volume of 4.8 L filled with 2.0 kg of activated carbon (Kuraray Coal GW48/100D, manufactured by Kuraray Chemical Co., Ltd.) and charged with ion-exchanged water, and simultaneously, a liquid having been treated with the activated carbon was obtained by being discharged from the lower part of the column. Subsequently, the liquid having been treated with the activated carbon, discharged from the lower part of the activated carbon column, was continuously supplied to a cation-exchange resin column having a volume of 2.0 L filled with 1.9 L of a cation-exchange resin (DIAION SK1BH, manufactured by Mitsubishi Rayon Aqua Solutions Co., Ltd.) and charged with ion-exchanged water, and simultaneously, an ion-exchanged liquid (pH: 3.0) was obtained by being taken out of the lower part of the column.

The resultant ion-exchanged liquid was concentrated at 60° C. to a 5 times concentration to provide a purified chlorogenic acid-containing composition. The resultant purified chlorogenic acid-containing composition was subjected to composition analysis and sensory evaluation. The results are shown in Table 1.

Reference Example 1

A sodium hydroxide aqueous solution having a concentration of 10% (w/w) was added to the purified chlorogenic acid-containing composition obtained in Comparative Example 1 to adjust the pH of the composition to 6, and then the resultant purified chlorogenic acid-containing composition was subjected to composition analysis and sensory evaluation. The results are shown in Table 1.

Example 1

A purified chlorogenic acid-containing composition was obtained in the same manner as in Comparative Example 1 except that the ion-exchanged liquid was concentrated to a 7 times concentration. The resultant purified chlorogenic acid-containing composition was subjected to composition analysis and sensory evaluation. The results are shown in Table 1.

Example 2

A purified chlorogenic acid-containing composition was obtained in the same manner as in Comparative Example 1 except that the ion-exchanged liquid was concentrated to a 10 times concentration. The resultant purified chlorogenic acid-containing composition was subjected to composition analysis and sensory evaluation. The results are shown in Table 1.

Example 3

A purified chlorogenic acid-containing composition was obtained in the same manner as in Comparative Example 1 except that the ion-exchanged liquid was concentrated to a 50 times concentration. The resultant purified chlorogenic acid-containing composition was subjected to composition analysis and sensory evaluation. The results are shown in Table 1.

Example 4

A glucose reagent (D(+)-glucose, manufactured by Wako Pure Chemical Industries, Ltd.) was added to the purified chlorogenic acid-containing composition obtained in Example 3 to adjust a "glucose/chlorogenic acid" mass ratio to 0.35, and then the resultant purified chlorogenic acid-containing composition was subjected to composition analysis and sensory evaluation. The results are shown in Table 1.

Example 5

The glucose reagent was added to the purified chlorogenic acid-containing composition obtained in Example 3 to adjust a "glucose/chlorogenic acid" mass ratio to 0.45, and then the resultant purified chlorogenic acid-containing composition was subjected to composition analysis and sensory evaluation. The results are shown in Table 1.

Comparative Example 2

The glucose reagent was added to the purified chlorogenic acid-containing composition obtained in Example 3 to adjust a "glucose/chlorogenic acid" mass ratio to 1.0, and then the resultant purified chlorogenic acid-containing composition was subjected to composition analysis and sensory evaluation. The results are shown in Table 1.

TABLE 1

| | | Comparative Example 1 | Example 1 | Example 2 | Example 3 |
|---|---|---|---|---|---|
| Production conditions | Raw material beans for chlorogenic acid-containing composition | Unground green beans | Unground green beans | Unground green beans | Unground green beans |
| | Chlorogenic acid in solids of chlorogenic acid-containing composition [mass %] | 30 | 30 | 30 | 30 |
| | pH | 3 | 3 | 3 | 3 |
| | Concentrating step and/or glucose addition step | 5 times concentration | 7 times concentration | 10 times concentration | 50 times concentration |
| Composition analysis | Chlorogenic acid in solids [mass %] | 45 | 45 | 45 | 45 |
| | Glucose in solids [mass %] | 4.0 | 5.4 | 6.3 | 6.8 |
| | Caffeine in solids [mass %] | 0.09 | 0.09 | 0.09 | Undetected |
| | Acetic acid in solids [mass %] | Undetected | Undetected | Undetected | 0.02 |
| | Malic acid in solids [mass %] | 1.4 | 1.4 | 1.4 | 1.4 |
| | Lipid content in solids [mass %] | Undetected | Undetected | Undetected | Undetected |
| | Glucose/chlorogenic acid [—] | 0.09 | 0.12 | 0.14 | 0.15 |
| | Caffeine/chlorogenic acid [—] | 0.002 | 0.002 | 0.002 | 0.000 |
| | Acetic acid/malic acid [—] | 0.000 | 0.000 | 0.000 | 0.015 |
| Sensory evaluation — Conditions | pH | 3 | 3 | 3 | 3 |
| | Chlorogenic acid concentration [%] | 0.3 | 0.3 | 0.3 | 0.3 |
| Item | Rough feeling on the tongue remaining after drinking (vs Comparative Example 1) | 0 | +1 | +2 | +2 |
| | Refreshing sourness (vs Example 8) | +2 | +2 | +2 | +2 |

| | | Example 4 | Example 5 | Comparative Example 2 | Reference Example 1 |
|---|---|---|---|---|---|
| Production conditions | Raw material beans for chlorogenic acid-containing composition | Unground green beans | Unground green beans | Unground green beans | Unground green beans |
| | Chlorogenic acid in solids of chlorogenic acid-containing composition [mass %] | 30 | 30 | 30 | 30 |
| | pH | 3 | 3 | 3 | 3 |
| | Concentrating step and/or glucose addition step | 50 times concentration + glucose addition | | | 5 times concentration |
| Composition analysis | Chlorogenic acid in solids [mass %] | 41 | 40 | 33 | 45 |
| | Glucose in solids [mass %] | 14.0 | 18.0 | 33.0 | 4.0 |
| | Caffeine in solids [mass %] | Undetected | Undetected | Undetected | 0.09 |
| | Acetic acid in solids [mass %] | 0.02 | 0.02 | 0.01 | Undetected |
| | Malic acid in solids [mass %] | 1.3 | 1.2 | 1.0 | 1.4 |

TABLE 1-continued

|  |  |  |  |  |  |  |
|---|---|---|---|---|---|---|
| | | Lipid content in solids [mass %] | Undetected | Undetected | Undetected | Undetected |
| | | Glucose/chlorogenic acid [—] | 0.35 | 0.45 | 1.00 | 0.09 |
| | | Caffeine/chlorogenic acid [—] | 0.000 | 0.000 | 0.000 | 0.002 |
| | | Acetic acid/malic acid [—] | 0.015 | 0.015 | 0.015 | 0.000 |
| Sensory evaluation | Conditions | pH | 3 | 3 | 3 | 6 |
| | | Chlorogenic acid concentration [%] | 0.3 | 0.3 | 0.3 | 0.3 |
| | Item | Rough feeling on the tongue remaining after drinking (vs Comparative Example 1) | +2 | +1 | 0 | +2 |
| | | Refreshing sourness (vs Example 8) | +2 | +2 | +2 | −1 |

Example 6

The glucose reagent was added to the purified chlorogenic acid-containing composition obtained in Comparative Example 1 to adjust a "glucose/chlorogenic acid" mass ratio to 0.12, and then the resultant purified chlorogenic acid-containing composition was subjected to composition analysis and sensory evaluation. The results are shown in Table 2 together with the results of Comparative Example 1.

TABLE 2

| | | Comparative Example 1 | Example 6 |
|---|---|---|---|
| Production conditions | Raw material beans for chlorogenic acid-containing composition | Unground green beans | Unground green beans |
| | Chlorogenic acid in solids of chlorogenic acid-containing composition [mass %] | 30 | 30 |
| | pH | 3 | 3 |
| | Concentrating step and/or glucose addition step | 5 times concentration | 5 times concentration + glucose addition |
| Composition analysis | Chlorogenic acid in solids [mass %] | 45 | 45 |
| | Glucose in solids [mass %] | 4.0 | 5.4 |
| | Caffeine in solids [mass %] | 0.09 | 0.09 |
| | Acetic acid in solids [mass %] | Undetected | Undetected |
| | Malic acid in solids [mass %] | 1.4 | 1.4 |
| | Lipid content in solids [mass %] | Undetected | Undetected |
| | Glucose/chlorogenic acid [-] | 0.09 | 0.12 |
| | Caffeine/chlorogenic acid [-] | 0.002 | 0.002 |
| | Acetic acid/malic acid [-] | 0 | 0 |
| Sensory evaluation | Conditions pH | 3 | 3 |
| | Chlorogenic acid concentration [%] | 0.3 | 0.3 |
| | Item Rough feeling on the tongue remaining after drinking (vs Comparative Example 1) | 0 | +1 |
| | Refreshing sourness (vs Example 8) | +2 | +2 |

Example 7

An acetic acid reagent (acetic acid, manufactured by Wako Pure Chemical Industries, Ltd.) was added to the purified chlorogenic acid-containing composition obtained in Example 3 to adjust an "acetic acid/malic acid" mass ratio to 0.2, and then the resultant purified chlorogenic acid-containing composition was subjected to composition analysis and sensory evaluation. The results are shown in Table 3 together with the results of Example 3.

Example 8

The acetic acid reagent was added to the purified chlorogenic acid-containing composition obtained in Example 3 to adjust an "acetic acid/malic acid" mass ratio to 0.35, and then the resultant purified chlorogenic acid-containing composition was subjected to composition analysis and sensory evaluation. The results are shown in Table 3 together with the results of Example 3.

Example 9

A malic acid reagent (DL-malic acid, manufactured by Wako Pure Chemical Industries, Ltd.) was added to the purified chlorogenic acid-containing composition obtained in Example 8 to adjust an "acetic acid/malic acid" mass ratio of 0.2, and then the resultant purified chlorogenic acid-containing composition was subjected to composition analysis and sensory evaluation. The results are shown in Table 3 together with the results of Example 3.

TABLE 3

|  |  | Example 3 | Example 7 | Example 8 | Example 9 |
|---|---|---|---|---|---|
| Production conditions | Raw material beans for chlorogenic acid-containing composition | Unground green beans | Unground green beans | Unground green beans | Unground green beans |
|  | Chlorogenic acid in solids of chlorogenic acid-containing composition [mass %] | 30 | 30 | 30 | 30 |
|  | pH | 3 | 3 | 3 | 3 |
|  | Concentrating step and/or glucose addition step | 50 times concentration | 50 times concentration | 50 times concentration | 50 times concentration |
|  | Step of adjusting organic acid ratio | None | Addition of acetic acid to Example 3 | Addition of acetic acid to Example 3 | Addition of malic acid to Example 8 |
| Composition analysis | Chlorogenic acid in solids [mass %] | 45 | 45 | 45 | 45 |
|  | Glucose in solids [mass %] | 6.8 | 6.8 | 6.8 | 6.8 |
|  | Caffeine in solids [mass %] | Undetected | Undetected | Undetected | Undetected |
|  | Acetic acid in solids [mass %] | 0.02 | 0.3 | 0.5 | 0.5 |
|  | Malic acid in solids [mass %] | 1.4 | 1.4 | 1.4 | 2.5 |
|  | Lipid content in solids [mass %] | Undetected | Undetected | Undetected | Undetected |
|  | Glucose/chlorogenic acid [—] | 0.15 | 0.15 | 0.15 | 0.15 |
|  | Caffeine/chlorogenic acid [—] | 0.000 | 0.000 | 0.000 | 0.000 |
|  | Acetic acid/malic acid [—] | 0.015 | 0.20 | 0.35 | 0.20 |
| Sensory evaluation | Conditions pH | 3 | 3 | 3 | 3 |
|  | Chlorogenic acid concentration [%] | 0.3 | 0.3 | 0.3 | 0.3 |
|  | Item Rough feeling on the tongue remaining after drinking (vs Comparative Example 1) | +2 | +2 | +2 | +2 |
|  | Refreshing sourness (vs Example 8) | +2 | +1 | 0 | +1 |

It is apparent from Tables 1 to 3 that the unpleasant feeling on the tongue that occurs specifically under an acidic condition can be improved by increasing the content of glucose and controlling the "glucose/chlorogenic acid" mass ratio and the "caffeine/chlorogenic acid" mass ratio within respective specific ranges in a purified chlorogenic acid-containing composition having its chlorogenic acid enriched. In addition, it is apparent from Table 3 that, when the composition of organic acids contains an excess of acetic acid, the refreshing feeling of an aftertaste is impaired, but the refreshing feeling of an aftertaste can be improved by increasing the ratio of malic acid.

The invention claimed is:

1. A purified chlorogenic acid-containing composition, having:
    a content of a chlorogenic acid in solids of from 10 mass % to 70 mass %;
    a mass ratio of glucose/chlorogenic acid of from 0.1 to 0.9;
    a mass ratio of caffeine/chlorogenic acid of 0.05 or less; and
    a pH of from 1 to 5.

2. The purified chlorogenic acid-containing composition according to claim 1, wherein the purified chlorogenic acid-containing composition further has a mass ratio of acetic acid/malic acid of from 0 to 0.3.

3. The purified chlorogenic acid-containing composition according to claim 1, wherein a content of a lipid in solids is from 0 mass % to 0.3 mass %.

4. The purified chlorogenic acid-containing composition according to claim 1, wherein the content of the chlorogenic acid in solids is from 20 mass % to 60 mass %.

5. The purified chlorogenic acid-containing composition according to claim 1, wherein the mass ratio of glucose/chlorogenic acid is from 0.12 to 0.45.

6. The purified chlorogenic acid-containing composition according to claim 1, wherein a content of glucose in solids is from 4.5 mass % to 30 mass %.

7. The purified chlorogenic acid-containing composition according to claim 1, wherein a content of caffeine in solids is 0.2 mass % or less.

8. The purified chlorogenic acid-containing composition according to claim 1, wherein a content of acetic acid in solids is 0.08 mass % or less.

9. The purified chlorogenic acid-containing composition according to claim 1, wherein the pH is from 2.5 to 4.5.

10. A method of producing a purified chlorogenic acid-containing composition, comprising:
    a first step of bringing a chlorogenic acid-containing composition into contact with at least one of adsorbent selected from the group consisting of activated carbon, acid clay, and activated clay; and
    a second step of subjecting the chlorogenic acid-containing composition after the contact with the adsorbent to at least one selected from the group consisting of the following steps (A) and (B) under an acidic condition:
    (A) a step of concentrating the chlorogenic acid-containing composition by 6 times or more at a temperature of from 20° C. to 70° C.; and (B) a step of adding glucose to the chlorogenic acid-containing composition.

11. The method of producing a purified chlorogenic acid-containing composition according to claim 10, wherein the acidic condition comprises a pH of from 1 to 5.

12. The method of producing a purified chlorogenic acid-containing composition according to claim 10, wherein the chlorogenic acid-containing composition comprises an extract of coffee beans.

13. The method of producing a purified chlorogenic acid-containing composition according to claim 12, wherein the coffee beans comprise at least one selected from the group consisting of green coffee beans, decaffeinated green coffee beans, roasted coffee beans having an L value of 45 or more, and decaffeinated roasted coffee beans having an L value of 25 or more.

14. The method of producing a purified chlorogenic acid-containing composition according to claim 12, wherein the coffee beans comprise at least one selected from the group consisting of unground coffee beans and ground coffee beans having an average particle size of from 0.3 mm to 7.5 mm.

15. The method of producing a purified chlorogenic acid-containing composition according to claim 12, wherein an extraction method for the extract of coffee beans comprises column extraction.

16. The method of producing a purified chlorogenic acid-containing composition according to claim 10, wherein the chlorogenic acid-containing composition to be used in the first step has a concentration of solids of 4.7 mass % or less.

17. The method of producing a purified chlorogenic acid-containing composition according to claim 10, wherein the chlorogenic acid-containing composition to be used in the first step has a content of a chlorogenic acid in solids of from 1 mass % to 70 mass %.

18. The method of producing a purified chlorogenic acid-containing composition according to claim 10, wherein the second step comprises subjecting the chlorogenic acid-containing composition to both the step (A) and the step (B).

19. The method of producing a purified chlorogenic acid-containing composition according to claim 10, wherein a concentration method in the step (A) comprises a normal-pressure concentration method or a reduced-pressure concentration method.

20. A method of producing a purified chlorogenic acid-containing composition, comprising:
a first step of bringing a chlorogenic acid-containing composition into contact with at least one of adsorbent selected from the group consisting of activated carbon, acid clay, and activated clay; and
a second step of subjecting the chlorogenic acid-containing composition after the contact with the adsorbent to at least one selected from the group consisting of the following steps (A) and (B) under an acidic condition of a pH of from 1 to 5:
(A) a step of concentrating the chlorogenic acid-containing composition by 6 times or more at a temperature of from 20° C. to 70° C. by using a normal-pressure concentration method or a reduced-pressure concentration method; and
(B) a step of adding glucose to the chlorogenic acid-containing composition, to adjust a mass ratio of glucose/chlorogenic acid to from 0.12 to 0.45.

* * * * *